United States Patent [19]

Schwartz et al.

[11] Patent Number: 4,697,023

[45] Date of Patent: Sep. 29, 1987

[54] PROCESS FOR THE PREPARATION OF OXY-DIPHTHALIC ANHYDRIDES

[75] Inventors: Willis T. Schwartz, Grand Island; Joseph A. Pawlak, Cheektowaga, both of N.Y.

[73] Assignee: Occidental Chemical Corporation, Niagara Falls, N.Y.

[21] Appl. No.: 914,955

[22] Filed: Oct. 3, 1986

[51] Int. Cl.$^4$ .......................................... C07D 307/89
[52] U.S. Cl. .................................................... 549/241
[58] Field of Search ......................................... 549/241

[56] References Cited

FOREIGN PATENT DOCUMENTS 122738 9/1980 Japan.
205232 9/1986 Japan.

OTHER PUBLICATIONS

Mitsui Toatsu Chemicals, Chemical Abstracts, vol. 94 (1981) 83799g.
Mitsui Toatsu Chemicals, Chemical Abstracts, vol. 94 (1981) 191,942g.

Primary Examiner—Richard L. Raymond
Attorney, Agent, or Firm—James F. Tao; Arthur S. Cookfair

[57] ABSTRACT

Oxy-diphthalic anhydrides are prepared by reacting a halophthalic anhydride with water and an alkali metal compound such as KF, CsF or $K_2CO_3$ in the presence of a polar, aprotic solvent.

24 Claims, No Drawings

PROCESS FOR THE PREPARATION OF OXY-DIPHTHALIC ANHYDRIDES

BACKGROUND OF THE INVENTION

This invention relates to a method for the preparation of oxy-diphthalic anhydrides. The products are useful chemical intermediates for the further preparation of various compounds such as the corresponding dicarboxylic acids and the various derivatives thereof, including for example, the salts, esters, acyl halides, amides, imides and the like. The oxy-diphthalic anhydrides are particularly useful as monomers in the preparation of polyimides, for example by polycondensation with a suitable diamine, such as ethylenediamine or phenylenediamine.

Various methods for the preparation of oxy-diphthalic anhydrides have been described in the chemical literature. In such method, shown to be useful in the preparation of oxy-diphthalic acids and anhydrides, involves the oxidation of tetramethyl diphenyl ethers. See Kolesnikov, G. S. et al *Vysokomol. Soyed*, A9, 612–18 (1967); Marvel, C. S. et al, *J. Am. Chem. Soc.* 80, 1197 (1958); and Latrova, Z. N. et al. *Volokna Sin. Polim.*, 15–24 (1970).

Three Japanese patents to Mitsui describe preparations based on reactions of substituted phthalic anhydrides. Japanese Patent Document 80/136, 246 (Chem. Abst. 95: 42680) teaches the coupling of 4-nitrophthalic anhydride in the presence of sodium nitrite to form oxy-diphthalic anhydride. In Japanese Patent Document 80/122, 738 (Chem. Abst. 94: 83799) Mitsui disclose the reaction of 4-halophthalic acid or anhydride with a base to yield oxy-diphthalic anhydride. In Japanese Patent Document 80/127, 343 (Chem. Abstr. 94: 191942) the reaction of 4-halo-phthalic anhydride, $Na_2CO_3$ and $NaNO_2$ in dimethyl sulfoxide to form 4,4'-dihydroxydiphthalylic anhydride is described.

German Pat. No. 2,416,594 (1975) discloses the coupling of 3-nitrophthalic anhydride in the presence of metal nitrites, such as sodium nitrite to form oxy-diphthalic anhydride.

Markezich, R. L. and Zamek, O. S. *J. Org. Chem.* 42, 3431 (1977) describe reaction of 4-nitrophthalimide with potassium fluoride in dimethylsulfoxide to form the corresponding oxy-diphthalimide which may be converted by hydrolysis to form the acid and ring closure to form the dianhydride.

SUMMARY OF THE INVENTION

It has now been found that diphthalic ether dianhydrides of the formula

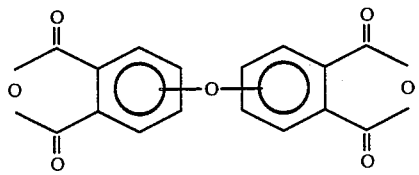

can be prepared by reacting a halo-phthalic anhydride of the formula

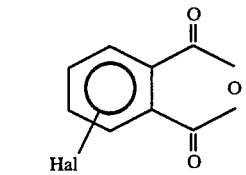

where Hal is F, Cl, Br or I, with water and an alkali metal compound selected from the group consisting of $KF$, $CsF$, and $K_2CO_3$ in the presence of a polar, aprotic solvent.

In the process of the invention, the halogen atom on the halophthalic anhydride reactant functions as a leaving group and becomes the site for the formation of the ether bridge. Thus when the reactant is a 4-halophthalic anhydride such as

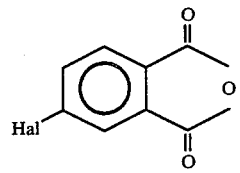

where Hal is F, Cl Br, or I, the oxy-diphthalic product will be 4,4'-oxy-diphthalic anhydride characterized by the formula

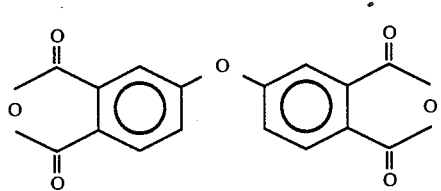

When the reactant is 3-halophthalic anhydride, the oxy-diphthalic product will be 3,3'-oxy-diphthalic anhydride, characterized by the formula

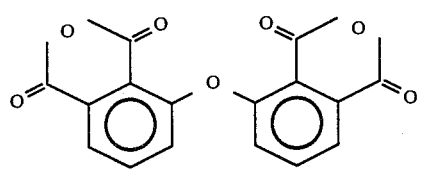

Alternatively, a mixture of the 3-halo- and 4-halophthalic anhydrides may be employed as the starting reactant, to form, in addition to the 4,4'- and 3,3'-oxy-diphthalic anhydride isomers, and a 3,4'-oxy-diphthalic anhydride of the formula

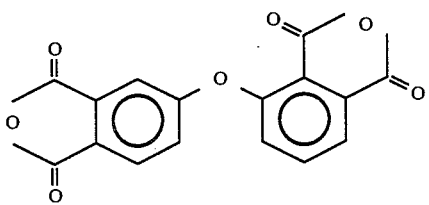

The halogen substituent on the starting halophthalic anhydride reactant may be F, Cl, Br or I. The preferred compound, based on economic as well as chemical considerations is 4-bromophthalic anhydride. The alkali metal compound may be potassium fluoride, cesium fluoride or potassium carbonate, the latter being preferred. The proportions of reactants may vary considerably, however, it is recommended that the alkali metal compound be employed in sufficient proportions to provide at least about one equivalent of potassium (or cesium) per mole of halo-phthalic anhydride. When chloro-phthalic anhydride or bromo-phthalic anhydride reactants are employed together with potassium fluoride or cesium fluoride, it has been found efficacious to provide at least about two equivalent, of alkali metal per mole of chloro- or bromo-phthalic anhydride. Preferably the alkali metal compound is employed in substantial excess, for example, up to about 50 percent excess, of the aforesaid equivalent proportions.

Water is a limiting reactant and ideally, for maximum efficiency, is preferably present in a molar proportion of $H_2O$:halophthalic anhydride of about 0.5. The water may be added to the initial reaction mixture or, alternatively, may be generated in-situ. For example, when potassium carbonate is employed in the reaction mixtures, a trace amount of water may be present in the initial reaction mixture and additional water generated in-situ as the reaction proceeds.

The process of the invention is preferably carried out at atmospheric pressure, but super-atmospheric pressure, for example under autogeneous conditions may be employed, if desired. The process is preferably carried out in the presence of a polar, aprotic solvent such as N-methyl-pyrrolidone, dimethyl formamide, dimethyl acetamide, triglyme, sulfolane, or the like. The preferred solvent is sulfolane.

The temperature at which the process is carried out may vary considerably, but will generally be within the range of about 120° to about 220° Celsius. Higher or lower temperature may be employed but are less efficient. The choice of solvent may govern the temperature employed. For example, at atmospheric conditions the boiling point of the solvent becomes a limiting condition. Moreover, the decrease in efficiency of the reaction as the temperature is lowered, varies somewhat with the solvent. When dimethyl formamide is employed the efficiency of the reaction decreases rapidly at temperatures below about 140° Celsius. The lower practical limit for the reaction in sulfolane is about 150° C. The preferred temperature is in the range of about 170°–210° and, most preferably, about 180°–190° Celsius. With certain solvents and/or extended reaction times there is an initial formation of oxy-diphthalic anhydride and then disappearance of the oxy-diphthalic anhydride with concurrent formation of hydroxy-phthalic anhydride. While not being bound by any particular theory, it is believed that cleavage of the ether may be occurring.

The following examples are provided to further illustrate this invention and the manner in which it may be carried out. It will be understood, however, that the specific details given in the examples have been chosen for purposes of illustration only and are not to be construed as limiting the invention. In the examples, unless otherwise indicated, all parts and percentages are by weight and all temperatures are in degrees Celsius.

EXAMPLE 1

To a solution of 12.5 parts of 4-fluorophthalic anhydride in 40.3 parts of sulfolane, was added 6.6 parts of potassium fluoride. The mixture was heated, with stirring, to 150° C. and 0.68 parts of water was added. The temperature was increased to about 180° C. and maintained thereat, with stirring, under a nitrogen atmosphere for a period of 4 hours. Samples of the reaction mixture were taken after two hours and 4 hours and analyzed by gas chromatographic techniques indicating, in area percent, 86.0 and 93.7 percent oxy-diphthalic anhydride.

EXAMPLE 2

The procedure of Example 1 was repeated except that the amount of water added was 0.34 parts. Analysis of samples taken after 1, 2, and 4 hours indicated, respectively, in area percent 52.3, 75.8, and 63.5 percent oxy-diphthalic anhydride.

EXAMPLE 3

The procedure of Example 1 was repeated except that the amount of water added was 0.16 parts. Gas chromatographic analysis of samples taken after 1, 2, and 4 hours indicated, respectively, in area percent 43.8, 43.1, and 43.2 percent oxy-diphthalic.

EXAMPLE 4

The procedure of Example 1 was repeated except that the amount of water added was 1.36 parts. Gas chromatographic analysis of samples taken after 2 hours and 4 hours indicated, respectively, in area percent, 88.7 and 85.5 percent oxy-diphthalic anhydride.

EXAMPLE 5

The procedure of Example 1 is repeated, except that in place of 4-fluorophthalic anhydride, there is substituted 3-fluorophthalic anhydride. The product formed is 3,3'-oxy-diphthalic anhydride.

EXAMPLE 6

The procedure of Example 1 is repeated, except that in place of 4-fluorophthalic anhydride, there is employed a mixture of 4-fluoro- and 3-fluorophthalic anhydrides with the resultant formation of a reaction product containing 4,4'-oxy-diphthalic anhydride, 3,3'-oxy-diphthalic anhydride, and 3,4'-oxy-diphthalic anhydride.

EXAMPLE 7

A mixture of 32.6 parts of 4-bromophthalic anhydride, 10.2 parts of potassium carbonate, 1.5 parts of Carbowax ®MPEG 2000 and a trace (i.e. less than about 0.1 parts) of water in 94.6 parts of sulfolane was heated to about 200° C. and and maintained thereat, with stirring, for about six hours. Samples were taken from the reaction mixture each hour, and analyzed by gas chromatographic techniques, with the following results.

| Reaction Time (Hours) | Oxy-Diphthalic Anhydride (G.C. Area %) |
| --- | --- |
| 1 | 0.9 |
| 2 | 25.1 |
| 3 | 55.8 |
| 4 | 79.0 |
| 5 | 85.2 |
| 6 | 86.3 |

EXAMPLE 8

A mixture of 27 parts of 4-chlorophthalic anhydride, 10 parts of potassium carbonate, 1.4 parts of Carbowax-®MPEG 2000 and a trace (less than about 0.1 part) of water in 65 parts of sulfolane was heated to about 200° C. and maintained thereat, with stirring, for about five hours. Samples were taken from the reaction mixture and analyzed by gas chromatographic techniques with the following results:

| Reaction Time (Hours) | Oxy-Diphthalic Anhydride (G.C. Area %) |
| --- | --- |
| 1 | 18.9 |
| 2 | 68.2 |
| 3 | 87.6 |
| 4 | 89.0 |
| 5 | 89.0 |

EXAMPLE 9

A mixture of 6.3 parts of 4-fluorophthalic anhydride and 8.65 parts of cesium fluoride in 40.3 parts of sulfolane was heated, with stirring to about 110° C. and 0.34 parts of water was added. The mixture was heated to about 180° C. and maintained thereat for 4 hours, with stirring, under an atmosphere of nitrogen. Analysis of the reaction mixture by gas chromatographic technique, indicated, in area percent, 95 percent oxy-diphthalic anhydride.

EXAMPLE 10

A mixture of 12.5 parts of fluorophthalic annydride and 6.6 parts of anhydrous potassium fluoride in 30.2 parts of N,N-dimethylformamide was heated, with stirring, to about 115° C. and 0.68 parts of water was added. The mixture was heated to about 154° C. and maintained thereat, under reflux conditions, with stirring, under a nitrogen atmosphere for about 4 hours. Analysis of the reaction mixture by gas chromatographic techniques indicated, in area percent, 57 percent 4,4'-oxy-diphthalic anhydride.

EXAMPLE 11

A mixture of 12.5 parts of 4-fluorophthalic anhydride and 6.6 parts of potassium fluoride in 30 parts of N,N-dimethylacetamide was heated, with stirring, to about 120° C. and 0.68 parts of water was added. The mixture was then heated to about 165° C. and maintained thereat, under reflux conditions, with stirring, under a nitrogen atmosphere for about 4 hours. Samples were taken after 1, 2 and 4 hours and analyzed by gas chromatographic techniques. The analyses indicated, in area percent, respectively, 47, 60, and 31 percent 4,4'-oxy-diphthalic anhydride.

EXAMPLE 12

A mixture of 632 parts of 4-fluorophthalic anhydride and 243 parts of potassium fluoride in 1368 parts of sulfolane was heated to 185° C. and 30.85 parts of water was added over a one hour period. The reaction mixture was maintained at about 185° C., with stirring, under an atmosphere of nitrogen for an additional 7 hours. Samples taken after 1, 3, 5, 7 and 8 hours were analyzed by gas chromatographic technique and found to contain, respectively, in area percent, 0, 1.6, 28, 60, and 93.6% 4,4'-oxy-diphthalic anhydride.

The solvent was removed by vacuum distillation. The residue was dissolved in sodium hydroxide, acidified with hydrochloric acid to a pH of about 1.0 to precipitate oxy-diphthalic acid, filtered, and the solid vacuum-dried. The dried solid was converted to the anhydride by refluxing in acetic anhydride. The pure 4,4'-oxy-diphthalic anhydride recovered by crystallization from the acetic anhydride, represented a yield of 74.1% of theory.

EXAMPLE 13

A mixture of 12.5 parts of 4-fluoro-phthalic anhydride and 6.6 parts of anhydrous potassium fluoride in 33 parts of N-methyl-2-pyrrolidone was heated to about 112° C. and 0.68 parts of water was added. The mixture was heated to about 170° C. and maintained thereat, with stirring, under an atmosphere of nitrogen, for a period of about 4 hours. Samples were taken after 1, 2, and 4 hours and analyzed by gas chromatographic techniques. The analyses indicated, in area percent, respectively, 67, 64, and 26 percent 4,4'-oxy-diphthalic anhydride.

EXAMPLE 14

The procedure Example 11 was repeated except that the temperature was maintained at about 152°–153° C. Analysis of samples taken after 1, 2, and 4 hours indicated 44, 51 and 8 percent 4,4'-oxy-diphthalic anhydride, respectively.

What is claimed is:

1. A process for the preparation of a diphthalic ether dianhydride of the formula

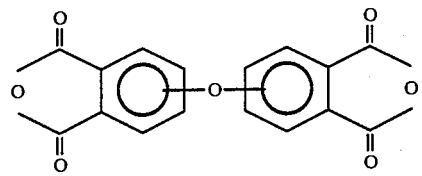

comprising reacting a halo-phthalic anhydride of the formula

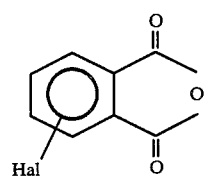

where Hal is F, Cl, Br or I, with water and an alkali metal compound selected from the group consisting of KF, CsF, and K₂CO₃ in the presence of polar, aprotic solvent.

2. A process according to claim 1 wherein the halophthalic anhydride is characterized by the formula

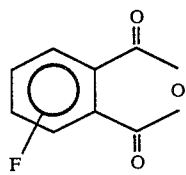

3. A process according to claim 1 wherein the halophthalic anhydride is characterized by the formula

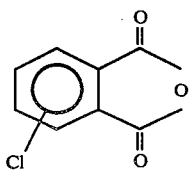

4. A process according to claim 1 wherein the halophthalic anhydride is characterized by the formula

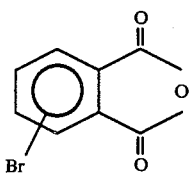

5. A process according to claim 1 wherein the alkali metal compound is potassium fluoride.

6. A process according to claim 1 wherein the alkali metal compounds is potassium carbonate.

7. A process according to claim 1 wherein the alkali metal compound is cesium fluoride.

8. A process according to claim 1 wherein the solvent is selected from the group consisting of sulfolane, N,N-dimethylformamide, N,N-dimethylacetamide, and N-methyl-2-pyrrolidone.

9. A process for the preparation of 4,4'-oxy-diphthalic anhydride which comprises reacting a 4-halophthalic anhydride with water in the presence of an alkali metal compound selected from the group consisting of potassium fluoride, cesium fluoride and potassium carbonate, in the presence of a polar, aprotic solvent.

10. A process according to claim 9 wherein the 4-halophthalic anhydride is 4-fluorophthalic anhydride.

11. A process according to claim 9 wherein the 4-halophthalic anhydride is 4-chlorophthalic anhydride.

12. A process according to claim 9 wherein the 4-halophthalic anhydride is 4-bromophthalic anhydride.

13. A process according to claim 10 wherein the alkali metal compound is potassium fluoride.

14. A process according to claim 10 wherein the alkali metal compound is cesium fluoride.

15. A process according to claim 10 wherein the alkali metal compound is potassium carbonate.

16. A process according to claim 11 wherein the alkali metal compound is potassium fluoride.

17. A process according to claim 11, wherein the alkali metal compound is cesium fluoride.

18. A process according to claim 11 wherein the alkali metal compound is potassium carbonate.

19. A process according to claim 12 wherein the alkali metal compound is potassium fluoride.

20. A process according to claim 12 wherein the alkali metal compound is cesium fluoride.

21. A process according to claim 12 wherein the alkali metal compound is potassium carbonate.

22. A process according to claim 9 wherein the solvent is selected from the group consisting of sulfolane, N,N-dimethylacetamide, N,N-dimethylformamide, and N-methyl-2-pyrrolidone.

23. A process according to claim 22 carried out at a temperature of about 170° to about 210° Celsius.

24. A process for the preparation of 4,4'-diphthalic ether dianhydride comprising reaction a 4-halo-phthalic anhydride wherein halo- is fluoro-, chloro-, or bromo- with water and an alkali metal compound selected from the group consisting of KF, CsF, and K₂CO₃ in the presence of a polar, aprotic solvent, selected from the group consisting of sulfolane, N,N-dimethyl formamide, N,N-dimethylacetamide, triglyme, and N-methyl-2-pyrrolidone at a temperature of about 150° to about 210° Celsius.

* * * * *